(12) United States Patent
Wolford et al.

(10) Patent No.: US 8,348,959 B2
(45) Date of Patent: Jan. 8, 2013

(54) ANGLED SURGICAL DRIVER

(75) Inventors: Todd A. Wolford, Goshen, IN (US);
Mark Nordman, Burket, IN (US);
Warren Scott Gareiss, Warsaw, IN (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 1988 days.

(21) Appl. No.: 11/387,282

(22) Filed: Mar. 23, 2006

(65) Prior Publication Data

US 2007/0225720 A1  Sep. 27, 2007

(51) Int. Cl.
*A61B 17/56* (2006.01)

(52) U.S. Cl. ........................................................ 606/104

(58) Field of Classification Search ................ 606/79; 81/177.6, 448–449; 623/42, 46, 50, 52
See application file for complete search history.

(56) References Cited

U.S. PATENT DOCUMENTS

| | | | |
|---|---|---|---|
| 1,398,116 A | 11/1921 | Root | |
| 2,570,706 A | 10/1951 | Peluse | 81/177 |
| 4,522,270 A | 6/1985 | Kishi | 173/163 |
| 4,578,083 A * | 3/1986 | Williams | 623/42 |
| 5,967,004 A | 10/1999 | Isbister | 81/177.2 |
| 6,050,989 A | 4/2000 | Fox et al. | 606/1 |
| 6,626,071 B2 | 9/2003 | Kesinger et al. | 81/437 |
| 6,875,218 B2 | 4/2005 | Dye et al. | 606/91 |
| 2004/0045417 A1* | 3/2004 | Chiu | 81/177.6 |
| 2004/0172036 A1 | 9/2004 | Dye | 606/81 |
| 2005/0159751 A1 | 7/2005 | Berthusen et al. | 606/80 |

FOREIGN PATENT DOCUMENTS

EP  1410763  4/2004

* cited by examiner

*Primary Examiner* — Alvin Stewart
*Assistant Examiner* — David Comstock
(74) *Attorney, Agent, or Firm* — Taylor IP, P.C.

(57) ABSTRACT

An angular surgical driver including a first rotatable member, a second rotatable member, an angled housing and a plurality of pins. The first rotatable member and second rotatable member are angularly associated with each other. The angled housing is rotatably connected to the first rotatable member and the second rotatable member. A plurality of pins drivingly connecting the first rotatable member to the second rotatable member.

19 Claims, 4 Drawing Sheets

ANGLED SURGICAL DRIVER

BACKGROUND OF THE INVENTION

1. Field of the Invention

The present invention relates to a surgical driver, and, more particularly, to an angled surgical driver.

2. Description of the Related Art

Joint replacement surgery has been used in the United States since as early as the 1960's. Implanting or repairing a prosthetic acetabular shell using a procedure of minimal invasive surgery requires screw hole plugs and screws that must be screwed in an acetabular shell. Bone screws are often driven through screw holes in the acetabular shell and into surrounding cortical bone to secure the shell to the bone. Screw hole openings in the acetabular shell are generally at an angle with respect to the surgical site, which often precludes a straight driving instrument from having the proper angle to reach the screw hole opening in the shell.

Minimally invasive surgical techniques have the advantage of reducing the trauma to tissue surrounding the surgical site during a surgical procedure. Often a reamer is required to prepare an implant site for the receipt of the acetabular shell, the reamer is connected to a driver, which is in turn connected to a rotational tool. The driver has a specific structure at the proximal (to the surgical site) end thereof, which is compatible with specific attachment mechanisms on the reamers.

An orthopaedic reamer assembly, which includes a driver, may also be used to shape an exterior surface of a bone. A rotary tool provides the motive force and is connected to the driver which is connected to the reamer. The driver generally has a shaft and a drive end. Orthopaedic reamer drivers are known which have a flexible shaft. The flexible shaft allows the reamer to travel along the path of a non-linear passage, such as an intramedullary canal, and thereby ream a non-linear opening.

It is known to have a drive body with L-shaped linking bars mounted between a drive body and a driven body with multiple L-shaped drive bars mounted therebetween. The drive body has a central linking hole with multiple mounting holes arranged around a periphery of the linking hole. As disclosed in United States Patent Application Publication No. US2004/0045417 A1.

What is needed in the art is a driving mechanism that doesn't require a central linking pin.

SUMMARY OF THE INVENTION

The present invention provides a pin-driven angled surgical driver.

The invention comprises, in one form thereof, an angular surgical driver including a first rotatable member, a second rotatable member, an angled housing and a plurality of pins. The first rotatable member and second rotatable member are angularly associated with each other. The angled housing is rotatably connected to the first rotatable member and the second rotatable member. A plurality of pins drivingly connects the first rotatable member to the second rotatable member.

An advantage of the present invention is that there is no central locating/linking pin.

Another advantage of the present invention is that each of the pins utilized are driving pins that transfer force from a first shaft to a second shaft.

Yet another advantage of the present invention is that the angled housing defines the rotatable angle between the two rotatable shafts.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
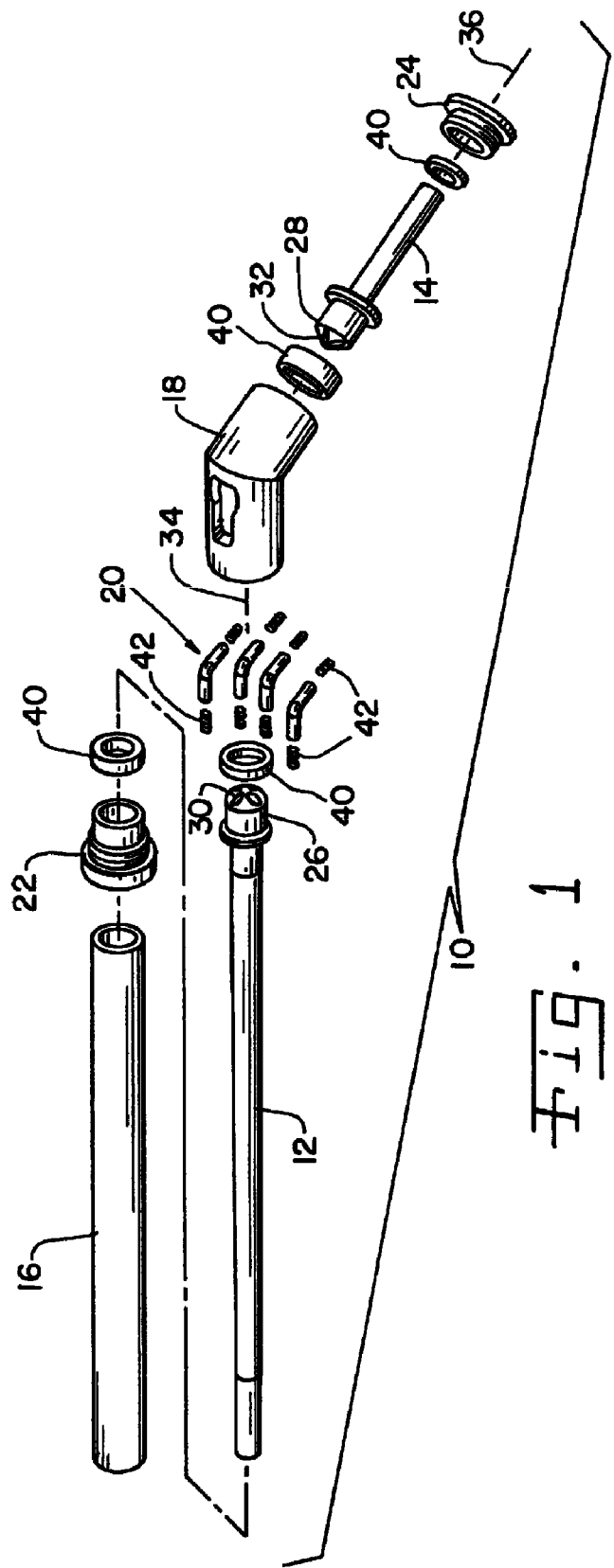
FIG. 1 illustrates an exploded perspective view of an embodiment of the surgical driver of the present invention.
Figure 2:
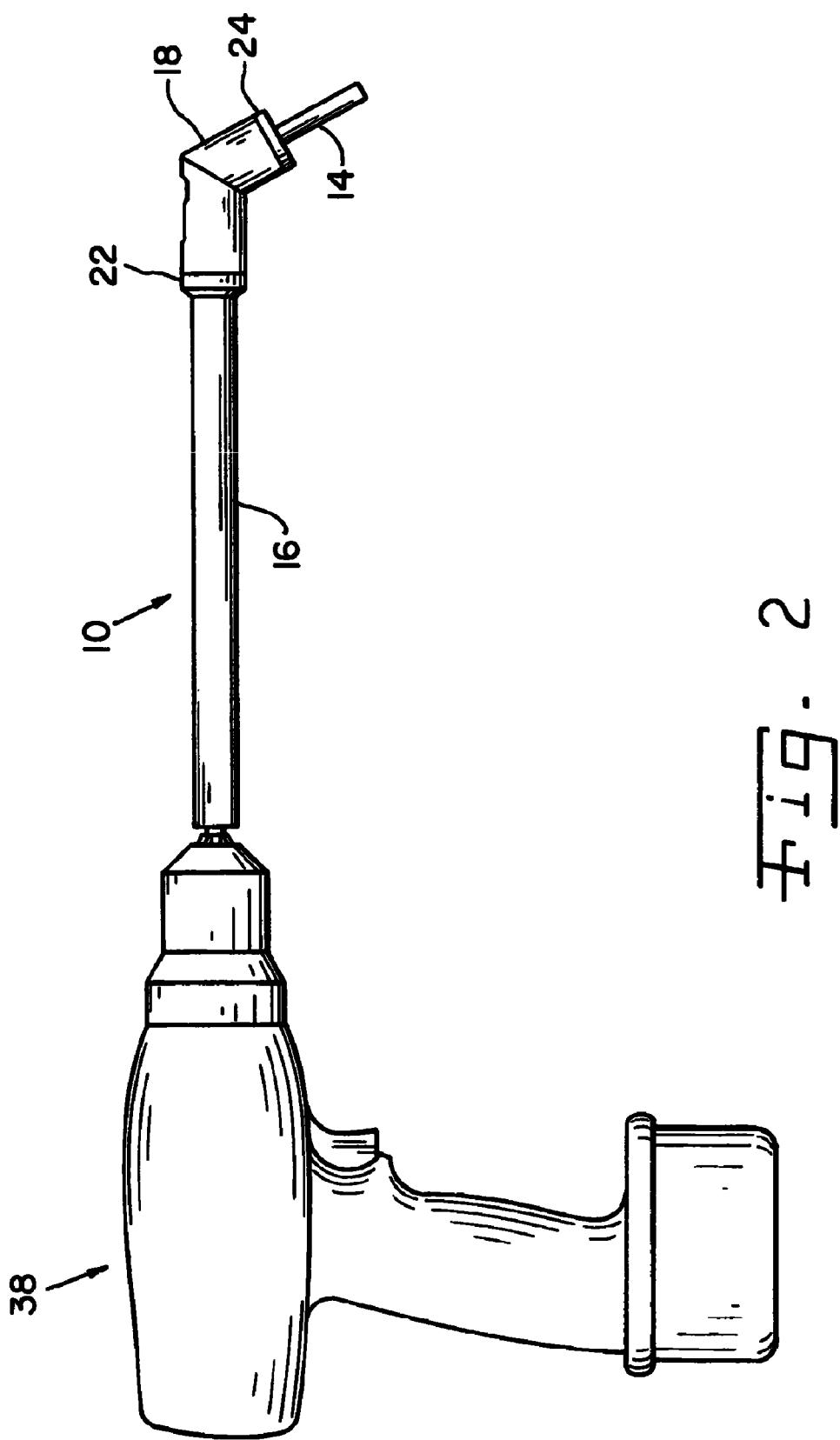
FIG. 2 shows the assembled surgical driver of FIG. 1.
Figure 3:
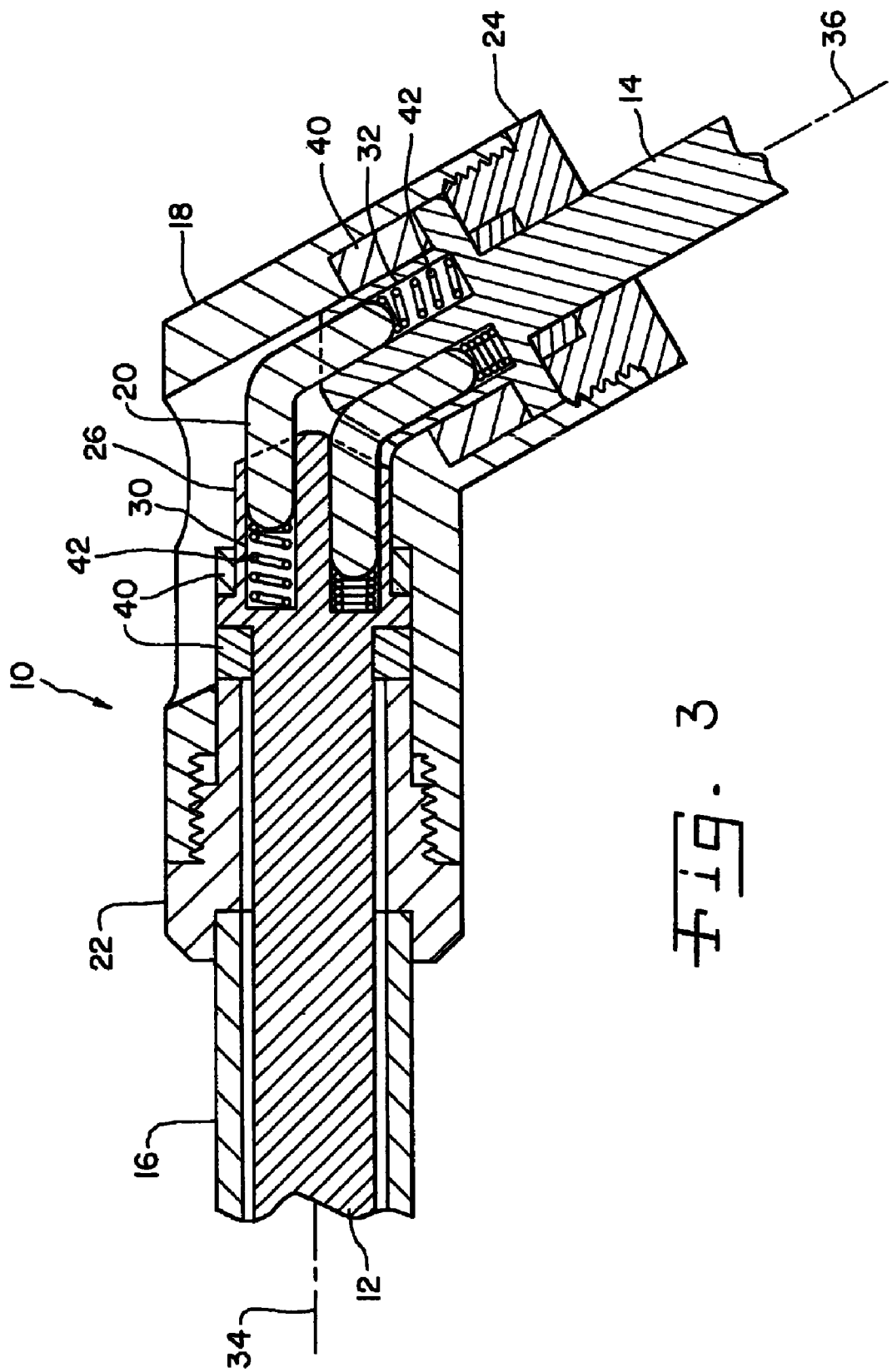
FIG. 3 is a sectioned view of a pin assembly of the surgical driver of FIGS. 1 and 2.
Figure 4:
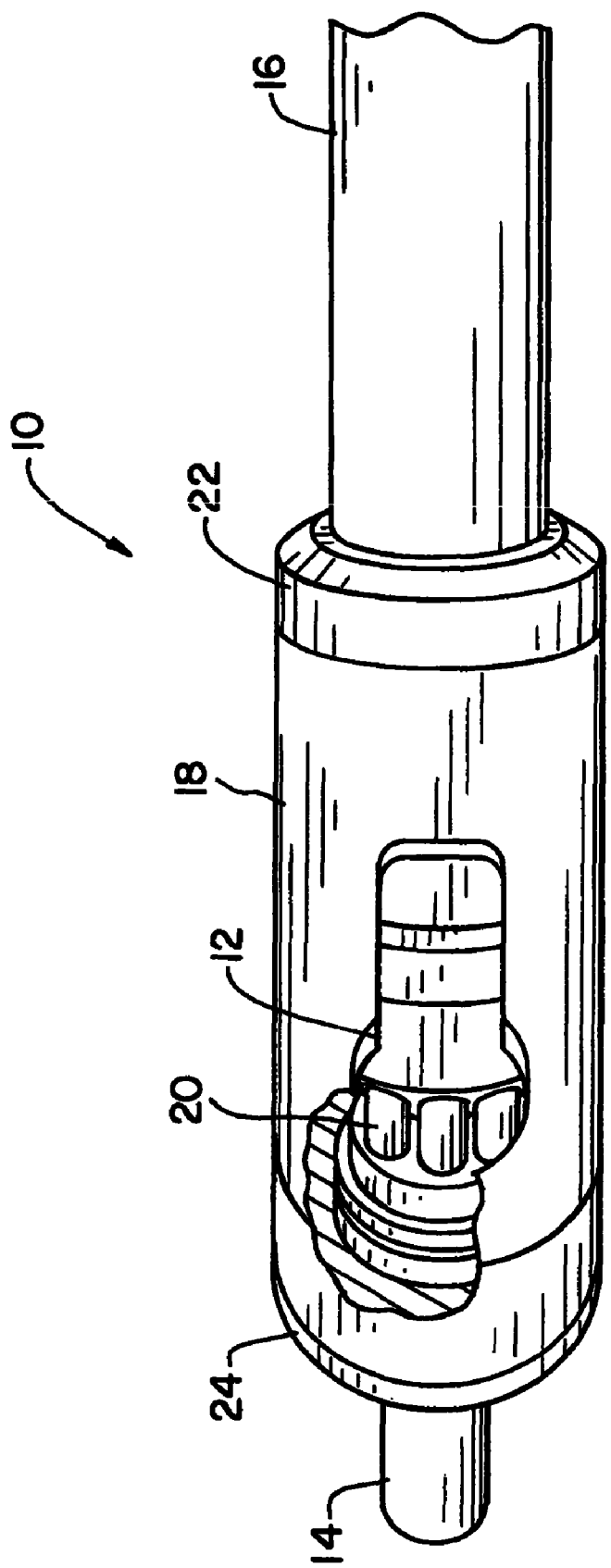
FIG. 4 is a partially sectioned view of the pin assembly of the surgical driver of FIGS. 1-3.

Referring now to the drawings, and more particularly to FIGS. 1-4, there is shown an angled surgical drive 10 including a shaft 12, a shaft 14, a sleeve 16, an angled housing 18, pins 20, and retaining collars 22 and 24. Shaft 12 rotates about an axis 34 and shaft 14 rotates about an axis 36. Sleeve 16 surrounds shaft 12 for a substantial length of shaft 12. Sleeve 16 is connected to angled housing 18 and provides a non-rotating surface that may be grasped by a surgeon while shaft 12 rotates therein. For the sake of clarity attachment features on the distal end of shaft 14 are omitted. Such features allow the attachment of cutting, boring, reaming and driving devices to shaft 14.

Pins 20 have an angle that is commensurate with the angle of angled housing 18. Pins 20 are generally cylindrical in nature being bent at approximately a midpoint thereof. Shaft 12 has a boss 26 with holes 30 therein. Shaft 14 has a boss 28 with holes 32 therein. Holes 30 and 32 are arranged around a periphery apart from axis 34 and axis 36 respectively. Holes 30 and 32 are spaced a predetermined distance from axis 34 and 36 respectively. Pins 20 are arranged to slide into holes 30 and 32 as shafts 12 and 14 are assembled to angled housing 18. Pins 20 are only retained in the assembly because shafts 12 and 14 are constrained to rotate at a fixed angle and distance to each other as determined by angled housing 18. A rotary power source 38 is connected to shaft 12 causing the rotation of shaft 12 with power being transferred by way of pins 20 to shaft 14. Springs 42 are positioned in holes 30 and 32 to control the movement of pins 20. Springs 42 are compressed as pins 20 move into holes 30 and 32, and expand as pins 20 extend within holes 30 and 32. Springs 42 cause pins 20 to be substantially equally biased away from shafts 12 and 14. Springs 42 lead to the smooth rotation of shafts 12 and 14 by causing pins 20 to extend equidistantly in holes 30 and 32 as shafts 12 and 14 rotate.

The presence of angled housing 18 precludes the need for any center retained pin that would be located on axis 34 and 36. This advantageously allows pins 20 to be spaced without concern of the location of a central hole and retaining pin in the assembly.

Retaining collars 22 and 24 are threadingly engaged with angled housing 18 and serve to position bosses 26 and 28 respectively with angled housing 18 and defines the axis about which shafts 12 and 14 rotate. Pins 20 are first inserted into either holes 30 or 32, which is then inserted into angled housing 18 then having an appropriate retaining collar 22 or 24 threaded into angled housing 18. Pins 20 are then aligned and inserted into holes 30 or 32, which remain to be filled as the remaining shaft is inserted into angled housing 18 with retaining collar 22 or 24 being installed thereon. Bearings 40, which are illustrated having differing sizes, rotationally support shafts 12 and 14. Features in housing 18 position bearings 40 to constrain shafts 12 and 14 to rotate relative to each other at a fixed distance from each other and at the angle determined by angled housing 18.

The assembly advantageously allows a smooth driving of shaft 14 with the transfer of power coming from shaft 12 by way of pins 20. Although four pins 20 are shown, any number of pins can be utilized in the assembly. Additionally, although pins 20 are illustrated as being equal distant from axis 34 and 36, such an arrangement is not required and an asymmetric arrangement is also contemplated as another embodiment of the present invention.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An angled surgical driver, comprising:
   a first rotatable member rotatable about a first rotational axis;
   a second rotatable member angularly associated with said first rotatable member, said second rotatable member being rotatable about a second rotational axis;
   an angled housing rotatably connected to said first rotatable member and said second rotatable member; and
   a plurality of pins drivingly connecting said first rotatable member to said second rotatable member, there being no pin located on both said first rotational axis and said second rotational axis.

2. The angled surgical driver of claim 1, wherein each of said plurality of pins include an angled bend.

3. The angled surgical driver of claim 2, wherein all of said plurality of pins are offset from said first rotational axis of said first rotatable member and from said second rotational axis of said second rotatable member.

4. The angled surgical driver of claim 3, wherein said angled housing defines said first rotational axis and said second rotational axis.

5. The angled surgical driver of claim 2, wherein said plurality of pins are cylindrical with said angled bend proximate to a mid section of each of said pins.

6. The angled surgical driver of claim 1, wherein said plurality of pins are slidingly associated with both said first rotatable member and said second rotatable member.

7. The angled surgical driver of claim 6, further comprising a plurality of springs including a first spring and a second spring, said plurality of pins including a first pin having a first end and a second end, said first spring biasing said first end in a direction away from said first rotatable member, said second spring biasing said second end in a direction away from said second rotatable member.

8. The angled surgical driver of claim 1, further comprising a collar that is removable from said angled housing, said collar having an axial opening through which a portion of said first rotatable member passes.

9. The angled surgical driver of claim 8, wherein said collar retains said first rotatable member to said angled housing.

10. The angled surgical driver of claim 9, wherein said collar is threadingly engaged with said angled housing.

11. The angled surgical driver of claim 10, further comprising another collar substantially similar to said collar, said other collar retaining said second rotatable member to said angled housing.

12. An angled surgical driver, comprising:
    a first rotatable member rotating about a first axis;
    a second rotatable member rotating about a second axis and being angularly associated with said first rotatable member; and
    a plurality of pins drivingly connecting said first rotatable member to said second rotatable member, there being no pin centered on both said first axis and said second axis.

13. The angled surgical driver of claim 12, further comprising an angled housing being rotatably connected to both said first rotatable member and said second rotatable member.

14. The angled surgical driver of claim 13, wherein each of said plurality of pins include an angled bend therein.

15. The angled surgical driver of claim 14, wherein said angled housing defines said first axis and said second axis.

16. The angled surgical driver of claim 15, wherein said pins are slidingly associated with both said first rotatable member and said second rotatable member.

17. The angled surgical driver of claim 16, wherein said plurality of pins are cylindrical with said angled bend proximate to a mid section of each of said pins.

18. The angled surgical driver of claim 15, further comprising a collar that is removably connected to said angled housing, said collar having an axial opening through which a portion of said first rotatable member passes.

19. The angled surgical driver of claim 18, wherein said collar retains said first rotatable member to said angled housing.

* * * * *